US010675395B2

(12) United States Patent
Anand et al.

(10) Patent No.: US 10,675,395 B2
(45) Date of Patent: Jun. 9, 2020

(54) PULMONARY-SYSTEMIC SHUNT DEVICES AND RELATED METHODS

(71) Applicants: Boston Scientific Scimed, Inc., Maple Grove, MN (US); Regents of the University of Minnesota, Minneapolis, MN (US)

(72) Inventors: Umang Anand, Plymouth, MN (US); Adam J. Black, Plymouth, MN (US); Ahmed Selim, Woodbury, MN (US); Steven D. Reinitz, Marlborough, MA (US); Bradley F. Slaker, Loretto, MN (US); Andrew D. Bicek, Elk River, MN (US); Paul F. Chouinard, Maple Grove, MN (US)

(73) Assignees: Boston Scientific Scimed, Inc., Maple Grove, MN (US); Regents of the University of Minnesota, Minneapolis, MN (US)

( * ) Notice: Subject to any disclaimer, the term of this patent is extended or adjusted under 35 U.S.C. 154(b) by 532 days.

(21) Appl. No.: 15/628,879

(22) Filed: Jun. 21, 2017

(65) Prior Publication Data
US 2017/0367820 A1 Dec. 28, 2017

Related U.S. Application Data

(60) Provisional application No. 62/353,969, filed on Jun. 23, 2016.

(51) Int. Cl.
*A61M 1/10* (2006.01)
*A61B 17/12* (2006.01)
(Continued)

(52) U.S. Cl.
CPC ............... *A61M 1/10* (2013.01); *A61B 17/11* (2013.01); *A61B 17/12036* (2013.01); *A61B 17/12109* (2013.01); *A61M 1/1008* (2014.02); *A61M 1/1037* (2013.01); *A61M 1/1039* (2014.02); *A61M 1/1081* (2013.01);
(Continued)

(58) Field of Classification Search
CPC .. A61M 17/12109; A61M 2017/00477; A61M 1/1008; A61M 1/122; A61M 1/3666; A61F 2/06
See application file for complete search history.

(56) References Cited

U.S. PATENT DOCUMENTS 5,261,878 A * 11/1993 Galindo ............. A61M 25/1011
604/103.1
5,437,601 A * 8/1995 Runge ................. A61M 1/3666
600/16

(Continued)

OTHER PUBLICATIONS

Jesse J. Esch, et al, Transcatheter Potts shunt creation in patients with severe pulmonary arterial hypertension: Initial clinical experience, 32 J. of Heart and Lung Transplantation 4, 381-387 (2013) (Year: 2013).*

*Primary Examiner* — Leslie R Deak
(74) *Attorney, Agent, or Firm* — Bookoff McAndrews, PLLC

(57) ABSTRACT

A method for treating a patient may include establishing an anastomosis between a pulmonary artery and an aorta; and pumping blood from the pulmonary artery to the aorta when the pulmonary artery has a pressure lower than or equal to a pressure of the aorta.

20 Claims, 3 Drawing Sheets

(51) Int. Cl.
*A61M 1/12* (2006.01)
*A61B 17/11* (2006.01)
(52) U.S. Cl.
CPC ...... *A61M 1/122* (2014.02); *A61B 2017/1107* (2013.01); *A61B 2017/1135* (2013.01)

(56) References Cited

U.S. PATENT DOCUMENTS

| | | | |
|---|---|---|---|
| 5,662,711 A | 9/1997 | Douglas | |
| 6,468,303 B1 * | 10/2002 | Amplatz | A61B 17/11 623/1.2 |
| 2004/0249335 A1 | 12/2004 | Faul et al. | |
| 2017/0216507 A1 * | 8/2017 | Kushwaha | A61M 1/127 |

* cited by examiner

PULMONARY-SYSTEMIC SHUNT DEVICES AND RELATED METHODS

CROSS-REFERENCE TO RELATED APPLICATIONS

This patent application claims the benefit of priority under 35 U.S.C. §119 to U.S. Provisional Patent Application No. 62/353,969, filed Jun. 23, 2016, which is herein incorporated by reference in its entirety.

BACKGROUND

Technical Field

Embodiments of the present disclosure relate generally to devices and methods for shunting blood within the vasculature to, for example, treat pulmonary hypertension.

Pulmonary hypertension is an increase in blood pressure of one or more portions of the lung vasculature. The lung vasculature includes the pulmonary arteries, pulmonary veins, and the pulmonary capillaries. The pulmonary arteries include the pulmonary trunk, which may be referred to generally as the pulmonary artery, and left and right pulmonary arteries that branch from the pulmonary trunk towards the lungs. The pulmonary veins include four veins, two extending between each lung and the left atrium of the heart.

Via the pulmonary circulation system, blood is pumped between the heart and the lungs, with deoxygenated blood flowing towards the lungs and oxygenated blood flowing towards the heart. Deoxygenated blood enters the right atrium of the heart from the systemic circulation system. It then flows to the right ventricle, which pumps the deoxygenated blood through the pulmonary arteries and into the pulmonary capillaries of the right and left lungs. From the lungs, oxygenated blood flows through the left and right pulmonary veins back towards the left atrium of the heart. The oxygenated blood then passes to the left ventricle, which pumps the blood through the aorta and to various organs via the systemic circulatory system.

There are a number of clinical groups of pulmonary hypertension, including pulmonary arterial hypertension, pulmonary hypertension due to lung disease, chronic thromboembolic pulmonary hypertension, pulmonary hypertension due to left heart disease, and pulmonary hypertension with unclear and/or multifactorial mechanisms. In some cases, increased pulmonary vascular resistance may increase the right ventricular afterload. This increased pressure can lead to right ventricle hypertrophy, systolic and/or diastolic dysfunction, and/or tricuspid regurgitation. Furthermore, left ventricular dysfunction and impaired cardiac output may occur due to leftward septal deviation, right-to-left dyssynchrony, and/or the anatomical interventricular dependence. Stress on the wall of the right ventricle and venous congestion may activate a neurohormonal and inflammatory response, which may increase the likelihood of heart failure.

One treatment method for severe pulmonary hypertension is an atrial septostomy, a procedure to create a connection between the right and left atria of the heart. This connection may reduce the preload of an overworked right ventricle. However, chronic hypoxemia (low concentration of oxygen in the blood) is a risk of the procedure, because oxygen-desaturated blood may travel from the right atrium to the left atrium and then may be delivered to the systemic circulatory system (e.g., to the heart, brain, and body).

Another treatment method for severe pulmonary hypertension is a Potts shunt procedure, which creates a connection between the left pulmonary artery and the descending aorta. This procedure may provide decompression of the right ventricle by allowing deoxygenated blood to bypass the pulmonary capillaries and travel directly to the systemic circulation system. However, for blood to flow from the pulmonary artery to the descending artery, the pressure in the pulmonary artery needs to be higher than the pressure of the aorta. Accordingly, the Potts shunt procedure is used for patients with suprasystemic pulmonary hypertension who are at risk for right heart failure.

SUMMARY

Examples of the present disclosure relate to, among other things, devices and methods for treating pulmonary hypertension. In some examples, the treatments may be used on patients having subsystemic pulmonary hypertension. Each of the examples disclosed herein may include one or more of the features described in connection with any of the other disclosed embodiments.

In one example, a method for treating a patient may include establishing an anastomosis between a pulmonary artery and an aorta; and pumping blood from the pulmonary artery to the aorta when the pulmonary artery has a lower pressure than a pressure of the aorta.

The method may additionally or alternatively include one or more of the following features or steps: establishing the anastomosis may include opening a ductus arteriosis; establishing the anastomosis may include using at least one tubular member to fluidly connect the pulmonary artery and the aorta; establishing the anastomosis may include creating a first opening in the pulmonary artery, creating a second opening in the aorta, and securing together the tissue surrounding the first and second openings; the anastomosis may include a valve; the method may further comprise implanting a pulsatile cuff around the pulmonary artery; the anastomosis may include a pump in fluid communication with the pulmonary artery and the aorta; the patient may have a mean pulmonary pressure between 50-80 mmHg, and a systemic pressure greater than the mean pulmonary pressure; and the patient may have subsystemic pulmonary hypertension, and the step of pumping blood may reduce a pulmonary pressure.

In another example, a method for treating a patient may include expanding an interior of a ligamentum arteriosum to form a patent ductus arteriosis; inserting a pump into the patent ductus arteriosis; and pumping blood from the pulmonary artery to the aorta, wherein the pulmonary artery has a lower pressure than a pressure of the aorta.

The method may additionally or alternatively include one or more of the following features or steps: the pump may be a constant flow pump; the expanding step may include inserting a balloon catheter into the interior of the ligamentum arteriosum; the method may further comprise inserting a tubular member into the patent ductus arteriosis to support the patent ductus arteriosis; the patient may have subsystemic pulmonary hypertension, and the step of pumping blood may reduce a pulmonary pressure.

In yet another example, a method for treating a patient may include fluidly connecting a first tubular member to a pulmonary artery; fluidly connecting a second tubular member to an aorta; coupling an end of the first tubular member and an end of the second tubular member to a pump; and pumping blood from the pulmonary artery to the aorta, wherein the pulmonary artery has a lower pressure than a pressure of the aorta.

The method may further include one or more of the following features or steps: the method may further comprise positioning the pump in at least one of a thoracic, abdominal, or pectoral space; the pump may be one of a constant flow pump or a pulsatile pump; the step of pumping blood may result in a decreased pulmonary pressure; the patient may have subsystemic pulmonary hypertension; and the patient may have a mean pulmonary pressure between 50-80 mmHg, and a systemic pressure greater than the mean pulmonary pressure.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

The present disclosure is drawn to devices and methods for treating, for example, pulmonary hypertension. In some examples, the treated patients have subsystemic hypertension, in which the pressure in the pulmonary artery is below or equal to the pressure in the aorta. Any of the components described herein may be inserted into the patient in a minimally invasive manner, such as during a laparoscopic procedure and/or through the patient's blood vessels. The devices may be delivered through catheters or other tubular members having a lumen.

Figure 1:
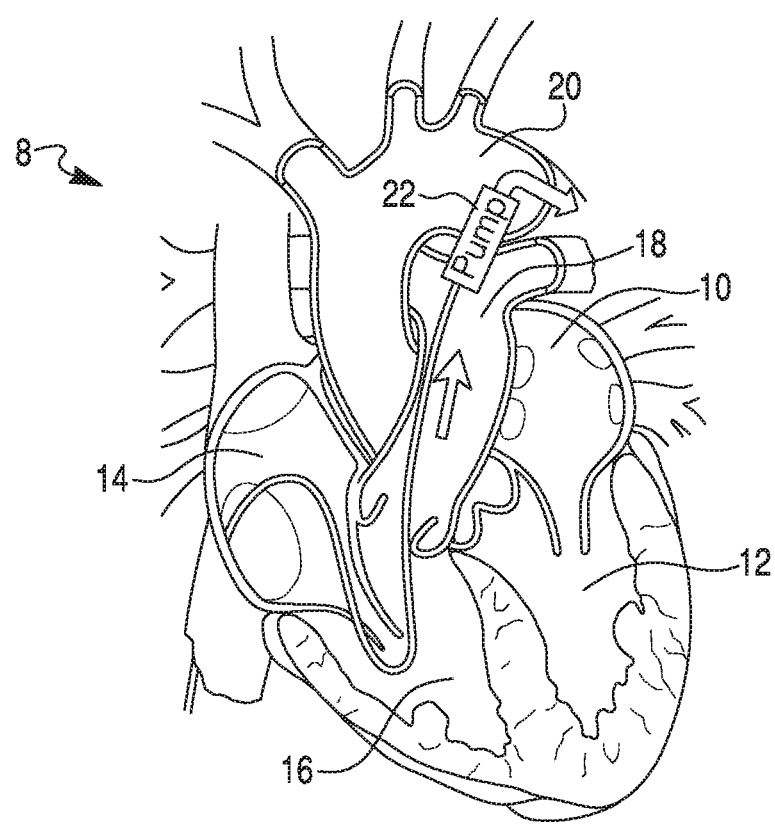
FIG. 1 illustrates a connection between the pulmonary artery and the aorta that includes a pump in a region of the ductus arteriosis, according to an example.

FIG. 1 illustrates a cross-sectional view of a heart 8. Heart 8 includes a left atrium 10, a left ventricle 12, a right atrium 14, and a right ventricle 16. The pulmonary artery 18 connects the right ventricle to the lungs. The aorta 20 connects the left ventricle to the organs of the body. In a procedure according to FIG. 1, an anastomosis may be created between pulmonary artery 18 and aorta 20 in a region of the ductus arteriosis.

Generally, the ductus arteriosis closes soon after a baby is born, leaving a ligament in its place (ligamentum arteriosum). To create the anastomosis shown in FIG. 1, the ligamentum arteriosum may be opened to recreate a patent ductus arteriosis. For example, a balloon catheter may be used to open the ligamentum arteriosum. The balloon catheter may be inserted through the patient's vasculature to reach the aorta wall or the pulmonary artery wall. The balloon catheter may then be inserted into an interior of the ligamentum arteriosum and used to open the ligamentum arteriosum into a patent ductus arteriosis. A stent or other tubular member may be inserted into the lumen and used to hold the ductus arteriosis in an open configuration.

Additionally or alternatively, a connection may be formed directly between the native walls of the pulmonary artery 18 and the aorta 20 adjacent to or in a region of the ductus arteriosis. For example, an opening may be created in each of the pulmonary artery 18 and the aorta 20, and the openings may be stitched together to form an anastomosis between the two vessels. In one exemplary procedure, a catheter with a magnet may be inserted into pulmonary artery 18, and another catheter with a magnet may be inserted into aorta 20. The magnets may be used to pull the two vessels towards each other. A needle or other sharp device then may be used to form holes in each vessel. The holes may be secured to each other with stitches, or a shunt may be used to maintain the connection.

Once a connection has been created between pulmonary artery 18 and aorta 20, a pump 22 may be inserted into the connection or otherwise placed in fluid communication with the pulmonary artery and aorta. For example, pump 22 may be inserted into the pulmonary artery (with pump outflow across the anastomosis) or in the aorta (with pump inflow across the anastomosis). The pump outflow or inflow may be channeled from or to the pump 22 via a cannula. The cannula may be expandable. In one example, pump 22 may be a constant flow pump. In other examples, pump 22 may be a pulsatile pump. Axial flow pumps, centrifugal flow pumps, hybrid or mixed-flow pumps, piston pumps, diaphragm pumps, or peristaltic pumps are other examples of pumps that may be capable of generating flow and the required pressure. Pump 22 may be inserted into the connection or into a vessel (e.g., pulmonary artery or aorta) using a minimally-invasive transcatheter delivery. Pump 22 may be secured to the interior of the anastomosis or vessel in any known manner, such as by a self-expanding portion or by adhesives. In one example, a lead may travel from pump 22 to a controller and/or power source positioned outside of the patient's body. In other examples, pump 22 may be controlled using wireless technology and/or may include a battery such as with transcutaneous energy transfer systems working on induction principles.

Figure 2:
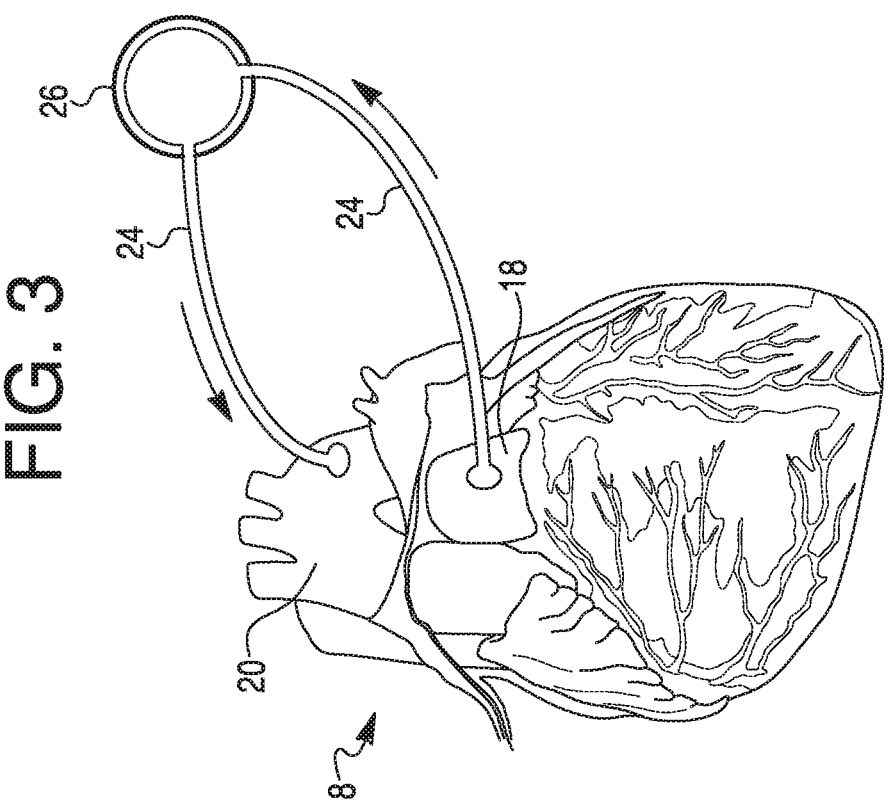
FIG. 2 illustrates a connection between the pulmonary artery and the aorta that includes a constant flow pump located in a different region than in FIG. 1, according to an example.

FIG. 2 illustrates an anastomosis between pulmonary artery 18 and aorta 20 that includes one or more tubular members 24 and pump 22. Each tubular member 24 may be fluidly coupled to and secured to one of the pulmonary artery 18 or aorta 20. In one example, tubular members 24 are secured to anterior regions of the respective vessels, as shown in FIG. 2. However, tubular members 24 may be secured to any suitable locations on pulmonary artery 18 and aorta 20. Accordingly, tubular members 24 may extend through a wall of their respective vessels. Tubular members 24 may be secured to the vessels using stitches, adhesive, or by any other method known to those in the art. Tubular members 24 may be thin, flexible tubes that include a biocompatible polymeric material. Pump 22 may be fluidly coupled to an end of each tubular member 24 and may pump blood from pulmonary artery 18 to aorta 20. Pump 22 may be any type of pump described in connection with FIG. 1. Pump 22 may be positioned outside of the heart, such as in the thoracic, abdominal, or pectoral spaces. In another example, the pump 22 may be located outside of the patient's body. Pump 22 may be located in any position that allows it to be in fluid communication with the pulmonary artery and the aorta. As in previous examples, pump 22 may be placed in the aorta or in the pulmonary artery.

Figure 3:
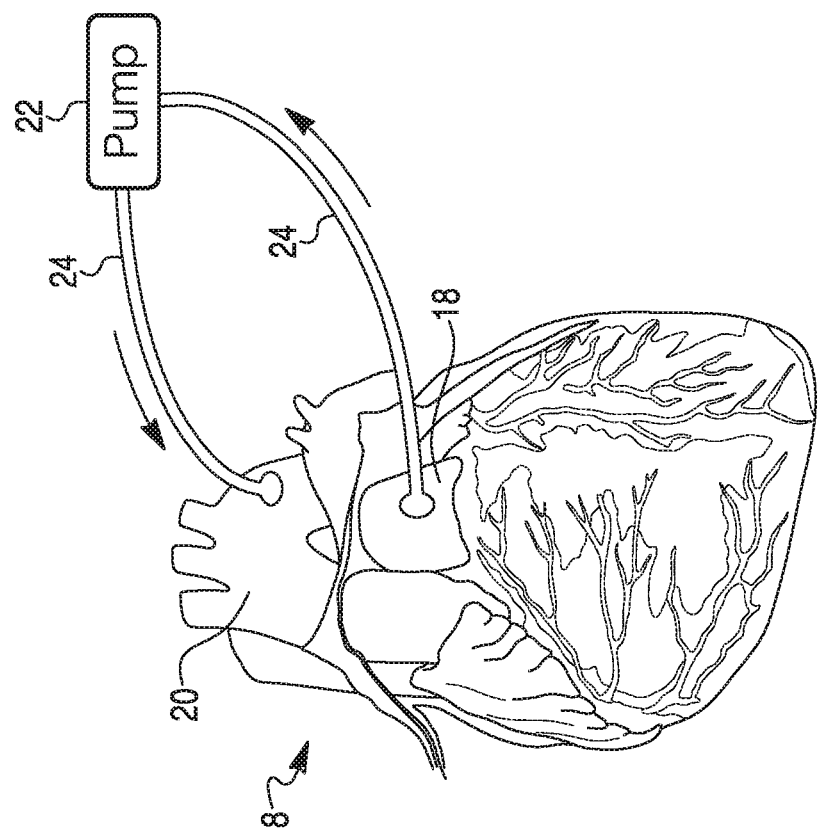
FIG. 3 illustrates a connection between the pulmonary artery and the aorta similar to FIG. 2 with a different type of pump, according to an example.

FIG. 3 illustrates a similar configuration as FIG. 2, except a pump 26 may be coupled to the two tubular members 24 instead of pump 22. In one example, pump 26 may be a counter-pulsatile pump. Accordingly, the pump may pump blood at varying RPMs, flow rates, and pressure heads depending on the patient's needs. Timing of the pumping may be optimally modulated with respect to the ECG signal from the heart. The ECG signal may be obtained by connecting a single lead to the right ventricle or another appropriate location in or on the heart. In one example, the pump 26 may draw blood from the pulmonary artery during systole, thus reducing the pulse pressure and maximum pressure on the pulmonary artery, and eject the blood into the aorta during diastole, thus increasing systemic diastolic pressure, increasing aortic root pressure, and aiding in coronary perfusion.

Figure 4:
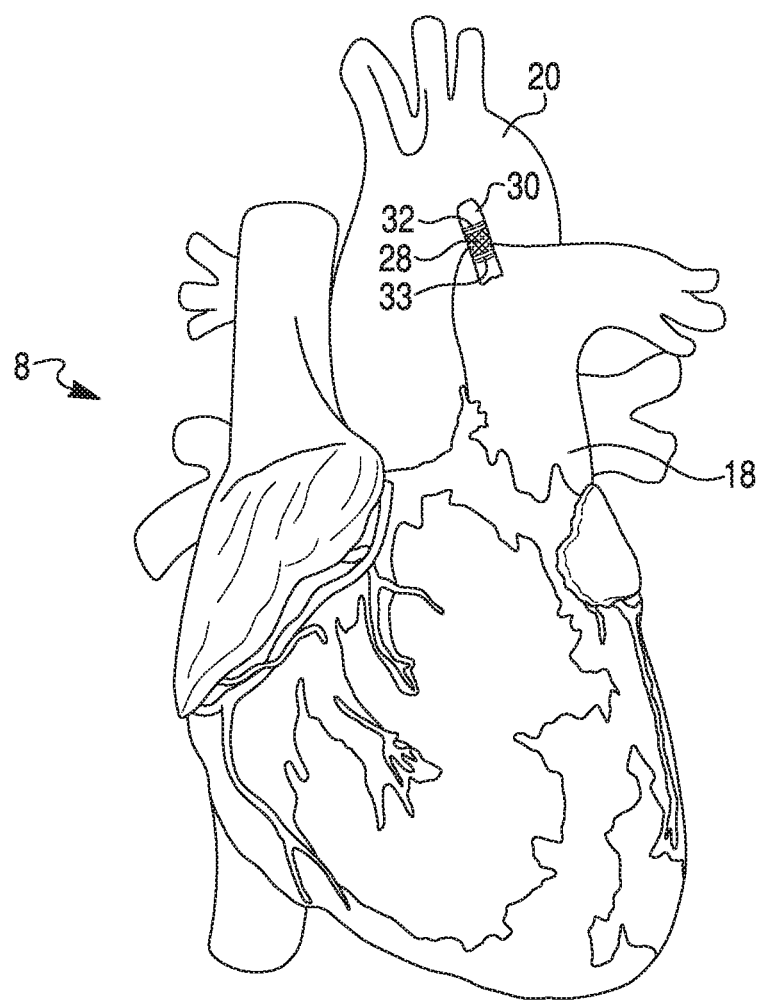
FIG. 4 illustrates a connection between the pulmonary artery and the aorta in a region of the ductus arteriosis with a pulsatile cuff around the pulmonary artery, according to an example.

FIG. 4 illustrates another example of an anastomosis between pulmonary artery 18 and aorta 20. In one example, the connection may include a tubular member 30 inserted into a patent ductus arteriosis or connecting the two vessels in a region of the ductus arteriosis. Tubular member 30 may include a polymeric material and may be stitched to openings in the vessel walls. In one example, the tubular member 30 may include valves 32 and 33. Valves 32 and 33 may be one-way valves that may allow blood flow from pulmonary artery 18 to aorta 20 but may prevent blood flow from aorta 20 to pulmonary artery 18. Valves 32 and 33 may be placed on either side of a cuff 28, which may be positioned around tubular member 30 to pump blood from pulmonary artery 18 to aorta 20. The cuff 28 may contract optimally based on the ECG signal of the heart. Cuff 28 may be implanted during a minimally invasive procedure, for example, through the patient's chest.

The procedures and devices described herein may be used on patients with pulmonary hypertension that may be sub-systemic (e.g., when pulmonary pressure is less than or equal to systemic pressure (e.g., aortic pressure)). In other words, the pulmonary hypertension is not suprasystemic (e.g., above the systemic (e.g., aortic) pressure). Patients with subsystemic hypertension cannot be treated with a passive shunt, such as a Potts shunt, between pulmonary artery 18 and aorta 20 because the blood would not flow naturally from the lower pressure pulmonary artery 18 to the higher pressure aorta 20. Accordingly, the procedures described herein may incorporate an active pump mechanism (e.g., constant flow pump, pulsatile pump, pulsatile cuff) to cause blood to flow from the lower pressure pulmonary artery 18 to the higher pressure aorta 20.

One of ordinary skill would not have considered the procedures described herein to treat subsystemic pulmonary hypertension because shifting blood from the pulmonary artery to the aorta shifts non-oxygenated blood to the systemic circulation. In patients that are candidates for a passive Potts shunt, the pulmonary artery pressure is so high and the symptoms are so severe that these terminal patients benefit from the procedure, even though their systemic blood oxygen level drops. In patients with pulmonary artery pressure that is subsystemic, the benefits of a connection between the pulmonary artery and aorta are not as clear, both because blood would not naturally flow and because causing flow from the pulmonary artery to the aorta would reduce blood oxygen levels. However, the procedures described herein may decrease the afterload of the right ventricle, which may prevent the progression of right ventricular failure—a main cause of death in patients with pulmonary hypertension. Additionally, the procedures described herein may include an anastomosis between the pulmonary artery and the descending aorta, such that oxygen saturation of the blood supplying the heart and brain (and upper extremities) may be unaffected. Accordingly, critical organs may be spared from ill effects one might expect from lower blood oxygen.

In a healthy patient, systemic pressure may be significantly higher than pulmonary pressure. For example, systemic pressure may be between 120-139 mmHg (systolic) and 80-89 mmHg (diastolic), and mean pulmonary pressure may be below 25 mmHg. A patient having subsystemic pulmonary hypertension, however, may have a mean pulmonary artery pressure between 50-80 mmHg, in some examples, and may have a systemic pressure that is greater than the mean pulmonary artery pressure.

The devices and methods described herein may reduce the right ventricle afterload by routing blood from the pulmonary circulation to the systemic circulation. When the right ventricle cannot pump effectively because of pulmonary hypertension, the patient may die of right heart failure. Relieving the pressure as described herein may therefore prevent right heart failure. Furthermore, the devices and methods may prevent weakening of the heart from overwork and/or facilitate reverse remodeling, during which the heart transitions back from a weakened state to a normal state.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A method for treating a patient, comprising:
   establishing an anastomosis between a pulmonary artery and an aorta; and
   pumping blood from the pulmonary artery to the aorta when the pulmonary artery has a pressure lower than or equal to a pressure of the aorta.

2. The method of claim 1, wherein establishing the anastomosis includes opening a ductus arteriosis.

3. The method of claim 1, wherein establishing the anastomosis includes using at least one tubular member to fluidly connect the pulmonary artery and the aorta.

4. The method of claim 1, wherein establishing the anastomosis includes creating a first opening in the pulmonary artery, creating a second opening in the aorta, and securing together the tissue surrounding the first and second openings.

5. The method of claim 1, wherein the anastomosis includes a valve.

6. The method of claim 1, further comprising implanting a pulsatile cuff around a tubular connection between the pulmonary artery and the aorta.

7. The method of claim 1, wherein the anastomosis includes a pump in fluid communication with the pulmonary artery and the aorta.

8. The method of claim 1, wherein the patient has a mean pulmonary pressure between 50-80 mmHg, and a systemic pressure greater than the mean pulmonary pressure.

9. The method of claim 1, wherein the patient has subsystemic pulmonary hypertension, and the step of pumping blood reduces a pulmonary pressure.

10. A method for treating a patient, comprising:
    expanding an interior of a ligamentum arteriosum to form a patent ductus arteriosis;
    inserting a pump into the patent ductus arteriosis; and
    pumping blood from the pulmonary artery to the aorta when the pulmonary artery has a pressure lower than or equal to a pressure of the aorta.

11. The method of claim 10, wherein the pump is a constant flow pump or a pulsatile pump.

12. The method of claim 10, wherein the expanding step includes inserting a balloon catheter into the interior of the ligamentum arteriosum.

13. The method of claim 10, further comprising inserting a tubular member into the patent ductus arteriosis to support the patent ductus arteriosis.

14. The method of claim 10, wherein the patient has subsystemic pulmonary hypertension, and the step of pumping blood reduces a pulmonary pressure.

15. A method for treating a patient, comprising:
    fluidly connecting a first tubular member to a pulmonary artery;
    fluidly connecting a second tubular member to an aorta;
    coupling an end of the first tubular member and an end of the second tubular member to a pump; and
    pumping blood from the pulmonary artery to the aorta when the pulmonary artery has a pressure lower than or equal to a pressure of the aorta.

16. The method of claim 15, further comprising positioning the pump in at least one of a thoracic, abdominal, or pectoral space.

17. The method of claim 15, wherein the pump is one of a constant flow pump or a pulsatile pump.

18. The method of claim 15, wherein the step of pumping blood results in a decreased pulmonary pressure.

19. The method of claim 15, wherein the patient has subsystemic pulmonary hypertension.

20. The method of claim 15, wherein the patient has a mean pulmonary pressure between 50-80 mmHg, and a systemic pressure greater than the mean pulmonary pressure.

* * * * *